United States Patent
Pfirrmann

(10) Patent No.: US 10,544,114 B2
(45) Date of Patent: Jan. 28, 2020

(54) PROCESS FOR PREPARING OXATHIAZIN-LIKE COMPOUNDS

(71) Applicant: GEISTLICH PHARMA AG, Wolhusen (CH)

(72) Inventor: Rolf W. Pfirrmann, Weggis (CH)

(73) Assignee: GEISTLICH PHARMA AG, Wolhusen (CH)

(*) Notice: Subject to any disclaimer, the term of this patent is extended or adjusted under 35 U.S.C. 154(b) by 0 days.

(21) Appl. No.: 16/091,596

(22) PCT Filed: Apr. 6, 2017

(86) PCT No.: PCT/IB2017/051992
§ 371 (c)(1),
(2) Date: Oct. 5, 2018

(87) PCT Pub. No.: WO2017/175177
PCT Pub. Date: Oct. 12, 2017

(65) Prior Publication Data
US 2019/0084950 A1    Mar. 21, 2019

Related U.S. Application Data

(60) Provisional application No. 62/319,675, filed on Apr. 7, 2016.

(51) Int. Cl.
C07D 291/06 (2006.01)
C07D 303/22 (2006.01)
C07D 303/32 (2006.01)
C07C 303/22 (2006.01)
C07C 303/32 (2006.01)

(52) U.S. Cl.
CPC .......... *C07D 291/06* (2013.01); *C07C 303/22* (2013.01); *C07C 303/32* (2013.01)

(58) Field of Classification Search
CPC .... C07C 303/22; C07C 303/32; C07D 291/06
See application file for complete search history.

(56) References Cited

U.S. PATENT DOCUMENTS 3,202,657 A    8/1965    Kuhne et al.

FOREIGN PATENT DOCUMENTS

WO    2013/190355 A1    12/2013
WO    2016098054 A1    6/2016

OTHER PUBLICATIONS

International Preliminary Report on Patentability issued for International Application No. PCT/IB2017/051992 dated Oct. 18, 2018, 9 pages.
Grunder-Klotz et al: "A conventient synthesis of 5-substituted tetrahydro-1,4,3-oxathiazines", Heterocycles Communication, Special I, Japan Institute of Heterocyclic Chemistry, JP, vol. 36, No. 4, Jan. 1, 1993, pp. 733-742.
Notification of Transmittal of the International Search Report and the Written Opinion of the International Searching Authority dated Jun. 26, 2017, cited in PCT/IB2017/051992, 16 pages.

*Primary Examiner* — Emily A Bernhardt
(74) *Attorney, Agent, or Firm* — Rothwell, Figg, Ernst & Manbeck, P.C.

(57) ABSTRACT

Oxathiazin-like compounds, processes for making new oxathiazin-like compounds, compounds useful for making oxathiazin-like compounds, and their uses are disclosed. Processes for efficient and safe manufacture of compounds useful for making oxathiazin-like compounds useful for treating patients suffering from cancers, bacterial infections, fungal infections and/or viral infections by administering oxathiazin-like compounds are also disclosed.

9 Claims, No Drawings

PROCESS FOR PREPARING OXATHIAZIN-LIKE COMPOUNDS

CROSS REFERENCE TO RELATED APPLICATION

This application is a 35 U.S.C. 371 National Phase Entry Application from PCT/IB2017/051992, filed Apr. 6, 2017, which claims the benefit of U.S. Patent Application No. 62/319,675 filed on Apr. 7, 2016, the disclosure of which is incorporated herein in its entirety by reference.

BACKGROUND OF THE INVENTION

Field of the Invention

The present invention relates to new compounds, processes for preparing new compounds and uses thereof.

Description of the Background Art

Oxathiazin-like compounds are known from U.S. Pat. Nos. 3,202,657 and 3,394,109.

There remains a need in the art for more efficient and safer processes for making such compounds to provide compounds with more potent antineoplastic and antimicrobial activity, less toxicity and side effects, and less resistance to treatment by tumor or microbial cells.

SUMMARY OF THE INVENTION

In accordance with the present invention, more efficient and safer processes for making new oxathiazin-like compounds, compounds useful for making oxathiazin-like compounds, and their uses are disclosed.

DETAILED DESCRIPTION OF THE INVENTION

According to certain embodiments, the present invention relates to highly efficient and safe processes and compounds for preparing oxathiazin-like compounds in steps, and derivatives thereof. Processes for making and using oxathiazin-like compounds (IUPAC Names: Tetrahydro-1,4,5-Oxathiazindioxid-4,4, or 1,4,5-Oxathiazandioxid-4,4) are disclosed in PCT/IB2015/059741, which is incorporated herein by reference in its entirety.

Oxathiazin-like compounds and derivatives thereof according to certain embodiments of the present invention have antineoplastic activities, antimicrobial activities and/or other activities.

Processes for making oxathiazin-like compounds and derivatives thereof according to certain embodiments of this invention provide advantageous methods for making compounds having antineoplastic activities, antimicrobial activities and/or other activities. In certain embodiments, oxathiazin-like compounds and derivatives thereof are useful, inter alia, in the treatment of cancers and tumors in a subject, such as a human patient. Accordingly, in certain embodiments the present invention also relates to treatment of cancers and tumors using compounds described herein. Cancers such as central nervous system cancers including glioblastoma, glioma, neuroblastoma, astrocytoma, and carcinomatous meningitis, colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, and metastases thereof, for example, are diseases contemplated for treatment according to certain embodiments of the invention. Drug resistant tumors, for example a multiple drug resistant (MDR) tumor, also are useful in certain embodiments using the inventive compounds, including drug resistant tumors which are solid tumors, non-solid tumors and lymphomas. It is presently believed that any neoplastic cell can be treated using the methods described herein.

In certain embodiments, exemplary compounds and processes for making compounds of the invention include the following:

Reacting isethionic acid or a salt thereof with benzyl alcohol to produce a compound having structure

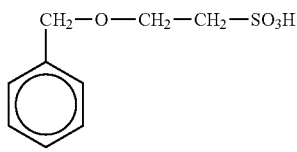

or a salt thereof. For example, a process may include:

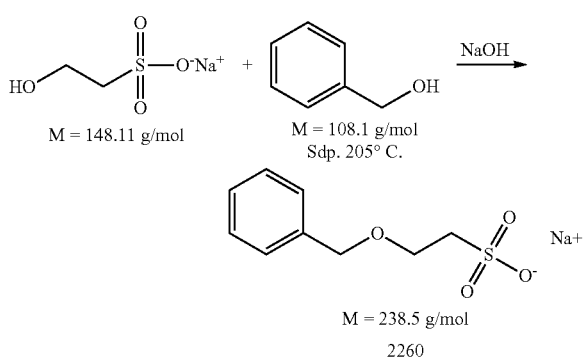

2260

In the foregoing reaction, isethionic acid sodium salt is reacted with benzyl alcohol in the presence of NaOH catalyst pellets (99%) to produce compound 2260 and water. The reaction is highly efficient and safe. The reaction of the present invention avoids the noxious odors and irritation caused by using reactants such benzyl chloride and/or elemental sodium.

In certain embodiments, a derivative of benzyl alcohol can be used, such as methylbenzyl alcohol, halogen (e.g., chloro) benzyl alcohol, methoxybenzyl alcohol or nitrobenzyl alcohol.

It was unexpected that one could achieve high purity and yield using the reaction of this disclosure. This disclosure describes a procedure that is commercially useful for producing large, e.g., 100-200 kg batches, with high yield, low toxicity, and economically.

In certain embodiments, the reaction may be carried out at a temperature of 200° C. or less, e.g., 160-190° C. or 170-180° C. The temperature can be reduced under vacuum, e.g., 130-140° C. at 100 mmHg.

In certain embodiments, the reaction time is 30 minutes to 5 hours including, e.g., 1, 2, 3, 4 or 5 hours or a fraction thereof.

The compounds may be in crystalline form, e.g., after crystallization and/or recrystallization in an alcohol, ketone, ester, or combination thereof. For example, the compounds of the present invention may be crystallized and/or recrystallized from an alcohol such as ethanol.

Synthesis of 2250

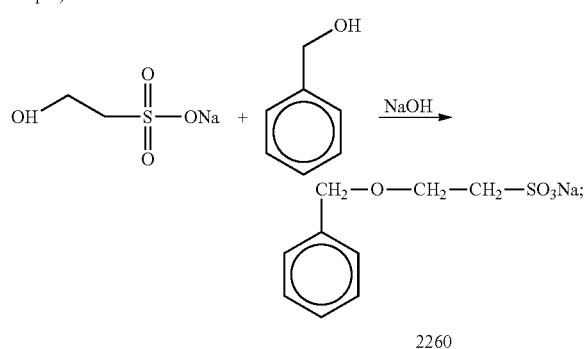
2250

Synthesis A

Step 1)

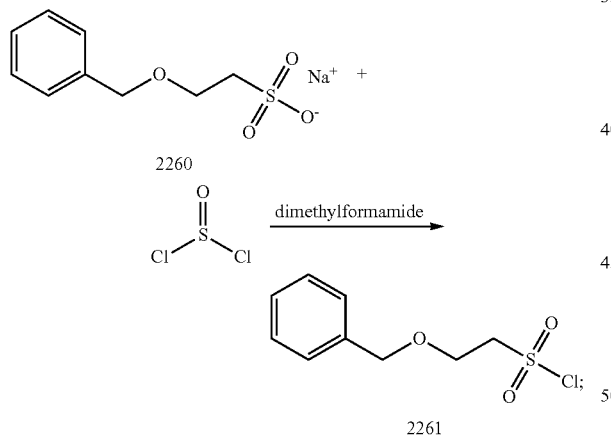
2260

Step 2)

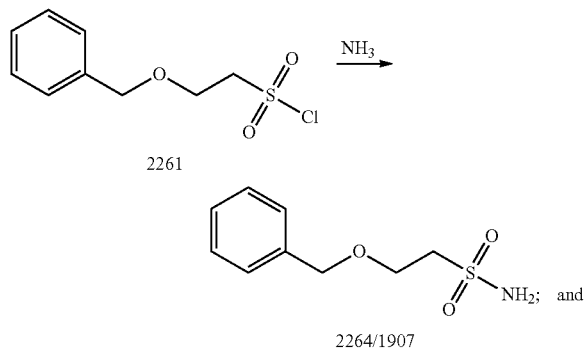
2260
2261

Step 3)

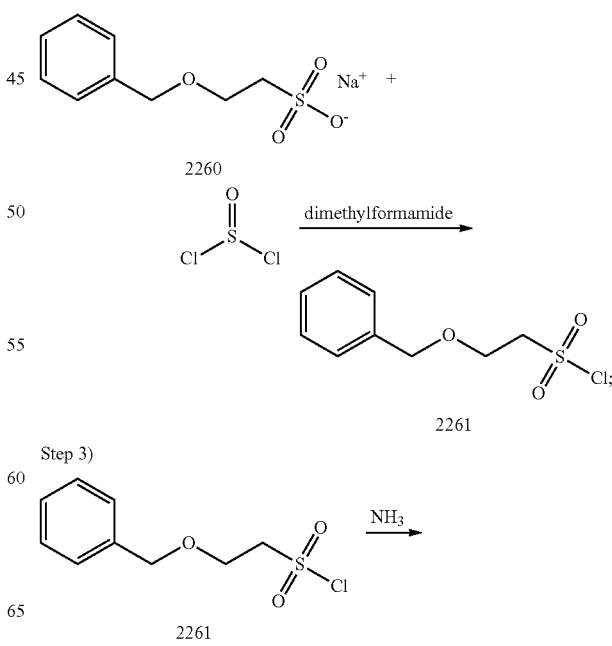
2261
2264/1907

Step 4)

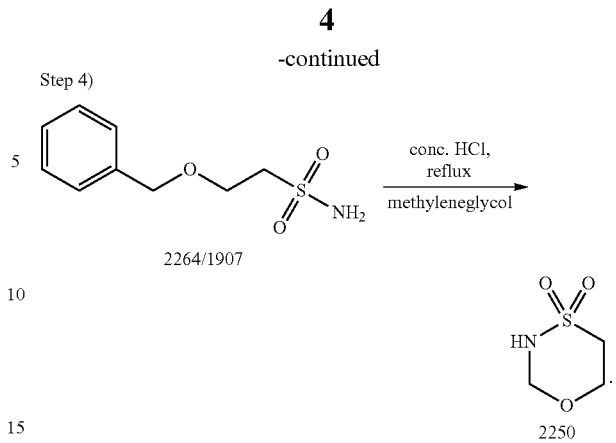
2264/1907
2250

Synthesis B

Step 1)

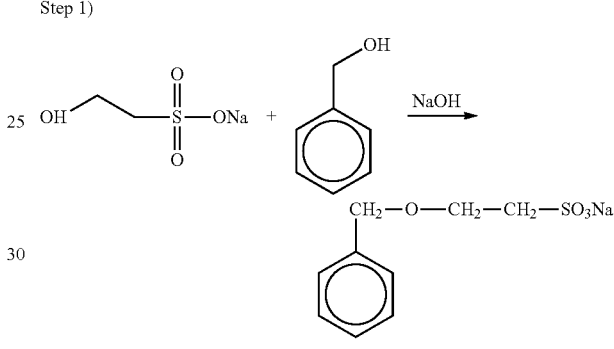
2260

Excess of benzyl alcohol by distillation of water under vacuum (e.g., at about 140° C., and about 100 mmHg vacuum);

Step 2)

2260
2261

Step 3)

2261

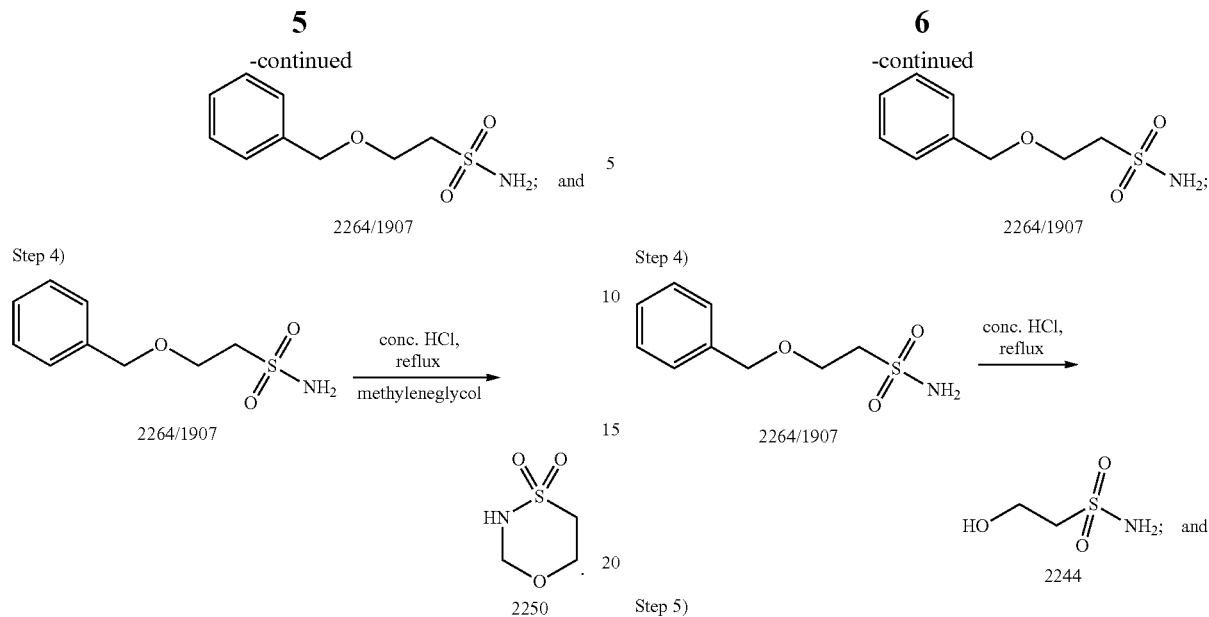

Synthesis C

Step 1)

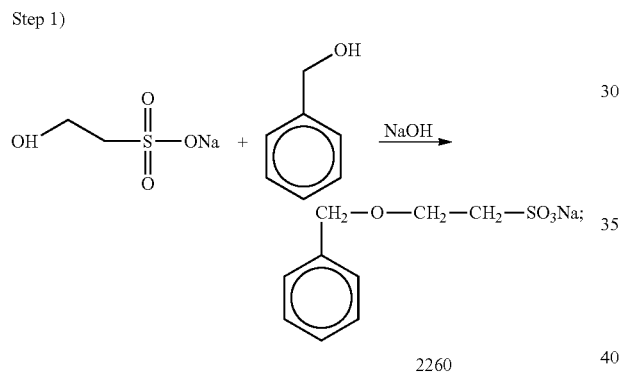

Step 2)

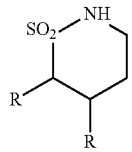

Step 3)

In one embodiment, substituted derivatives compound 2250 may be prepared by modifying the foregoing processes. Substituted derivatives of compound 2250 include:

Wherein R may be H or alkyl or aryl. In certain embodiments, R is a $C_1$ to $C_6$ alkyl. R may be methyl, ethyl, propyl, butyl, cyclohexyl, methylcyclohexyl, benzyl, phenyl, nitrophenyl, carbethoxyphenyl, methylphenyl, nitro-phenyl or naphthyl radical. In certain embodiments, R is methyl.

More specifically, the present disclosure relates to the materials, products and methods described below. This invention is illustrated by the following examples which are merely for the purpose of illustration and are not to be regarded as limiting the scope of the invention or the manner in which it can be practiced.

Example 1

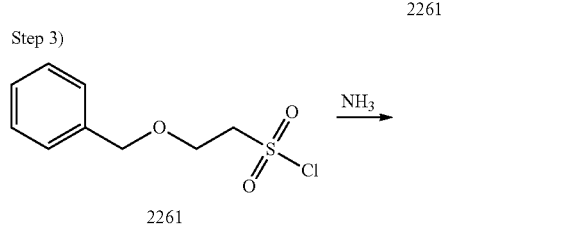
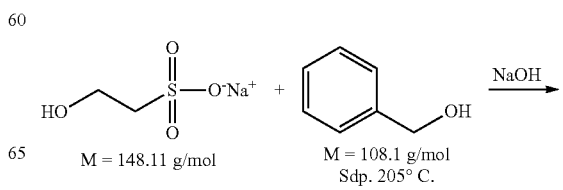

-continued

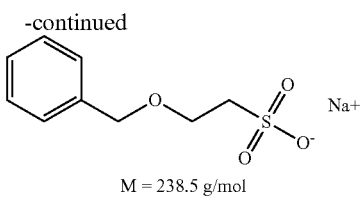

M = 238.5 g/mol 14.8 g Isethionic acid-Na and
150 mg NaOH and
100 ml of benzyl alcohol were reacted in a 250 ml round bottom flask with a distillation bridge and heated slowly at 180 to 200° C. for about 3 hours. At this temperature, about 1.8 g of water was distilled off.
The reaction product was allowed to cool, forming crystals, and then filtered under suction. The very fine precipitate was dried.
18.7 g of a white substance at 78.6% yield was recovered.
IR confirmed that the reaction product was 99% pure.

Example 2

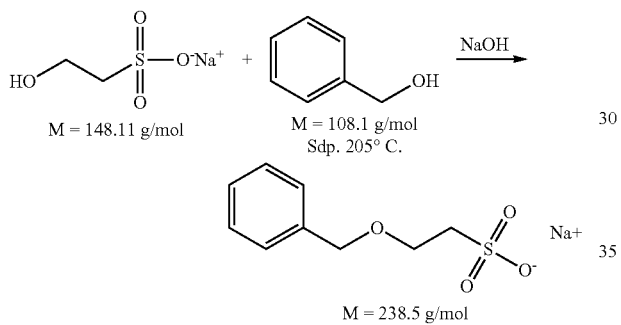

Isethionic acid sodium salt and NaOH pellets in an excess of Benzyl alcohol are heated in a glass flask to about 170-180° C. About 1 mole of water was distilled off. The remainder is cooled, then acetic ester or petroleum ether is added. The material is drawn through filter paper under suction, leaving 98% pure product.

Typically the reaction can be carried out at temperatures within a range of about 160-190° C. until the reactants are in solution. Benzyl alcohol has a boiling point of about 205° C. Thus, at the typical reaction temperatures, it is possible to boil off any water that is produced without negatively affecting the reaction. As noted above, the reaction can take place under vacuum at lower temperatures, e.g., in an excess of benzyl alcohol or an active derivative thereof, with distillation of water under partial vacuum (e.g., at about 130-140° C., and about 100 mmHg vacuum).

While the invention has been shown or described in only some of its embodiments, it should be apparent to those skilled in the art that it is not so limited, but is susceptible to various changes without departing from the spirit and scope of the invention. Furthermore, it is to be understood that the form of the invention shown and described is to be taken as presently preferred embodiments. Various modifications and changes may be made to each and every processing step as would be obvious to a person skilled in the art having the benefit of this disclosure. It is intended that the following claims be interpreted to embrace all such modifications and changes and, accordingly, the specification is to be regarded in an illustrative rather than a restrictive sense. The disclosure, including any readily discernible variants of the teachings herein, defines, in part, the scope of the foregoing claim terminology such that no inventive subject matter is dedicated to the public. Moreover, it is intended that the appended claims be construed to include alternative embodiments.

The invention claimed is:

1. A process comprising reacting isethionic acid or a salt thereof with benzyl alcohol to produce a compound having structure

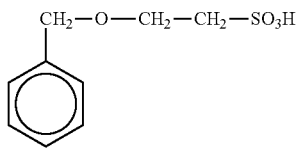

or a salt thereof.

2. The process of claim 1, comprising using sodium hydroxide as a catalyst.

3. The process of claim 1, wherein the salt of isethionic acid is isethionic acid sodium salt.

4. The process of claim 1, wherein

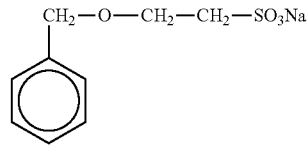

is produced.

5. A process for preparing compound 2250 comprising the following reaction steps:

a)

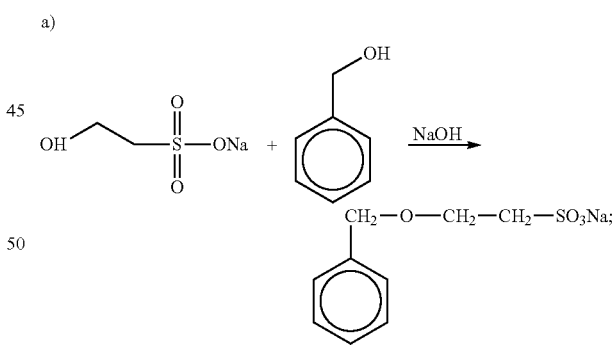

2260 b)

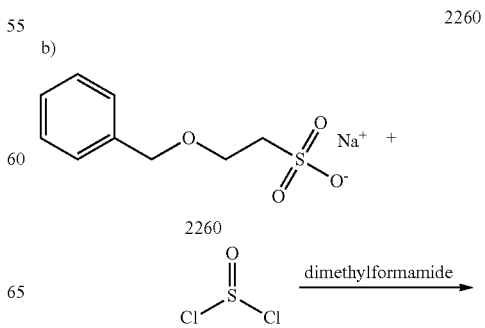

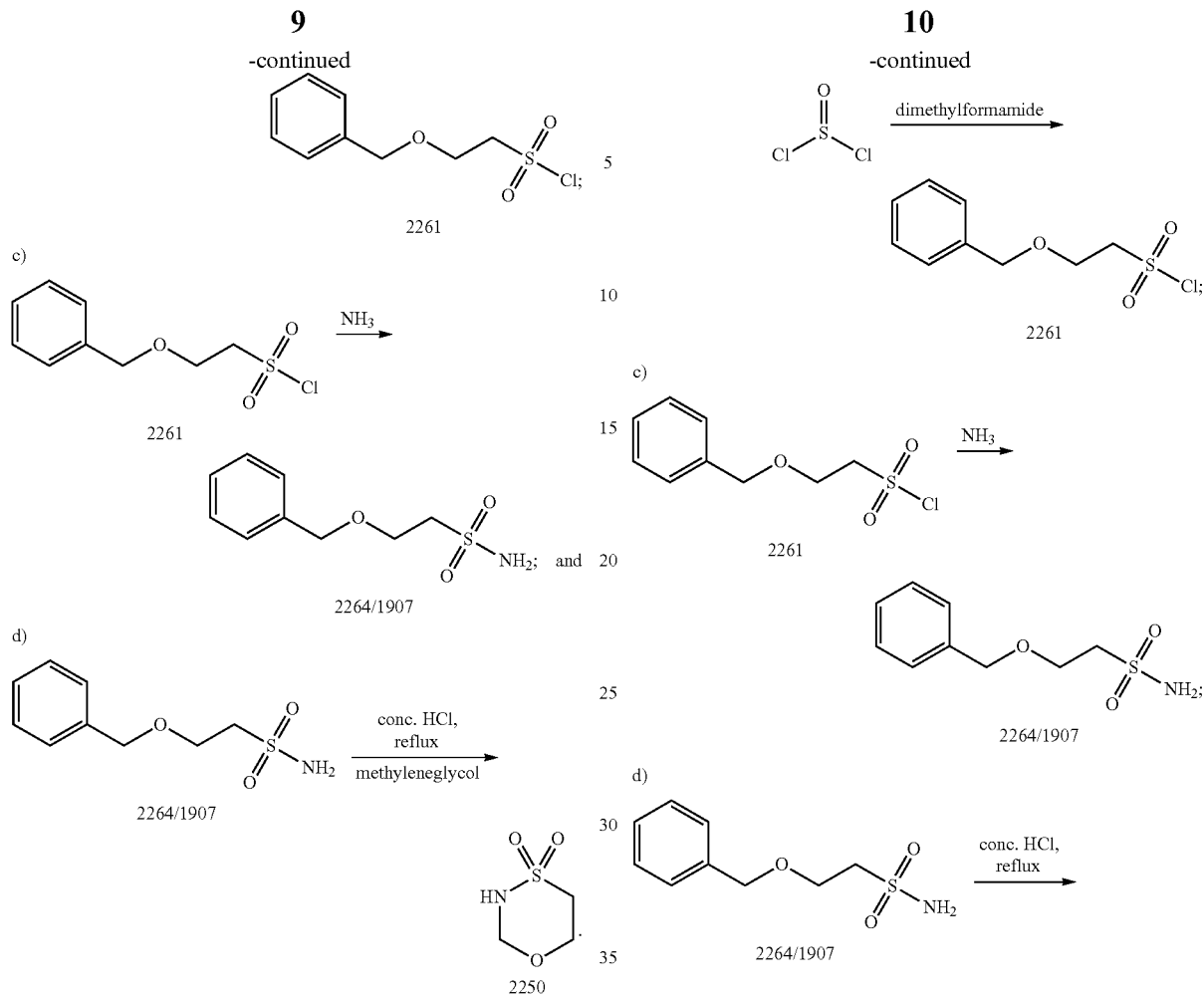
6. A process for preparing compound 2250 comprising the following reaction steps:
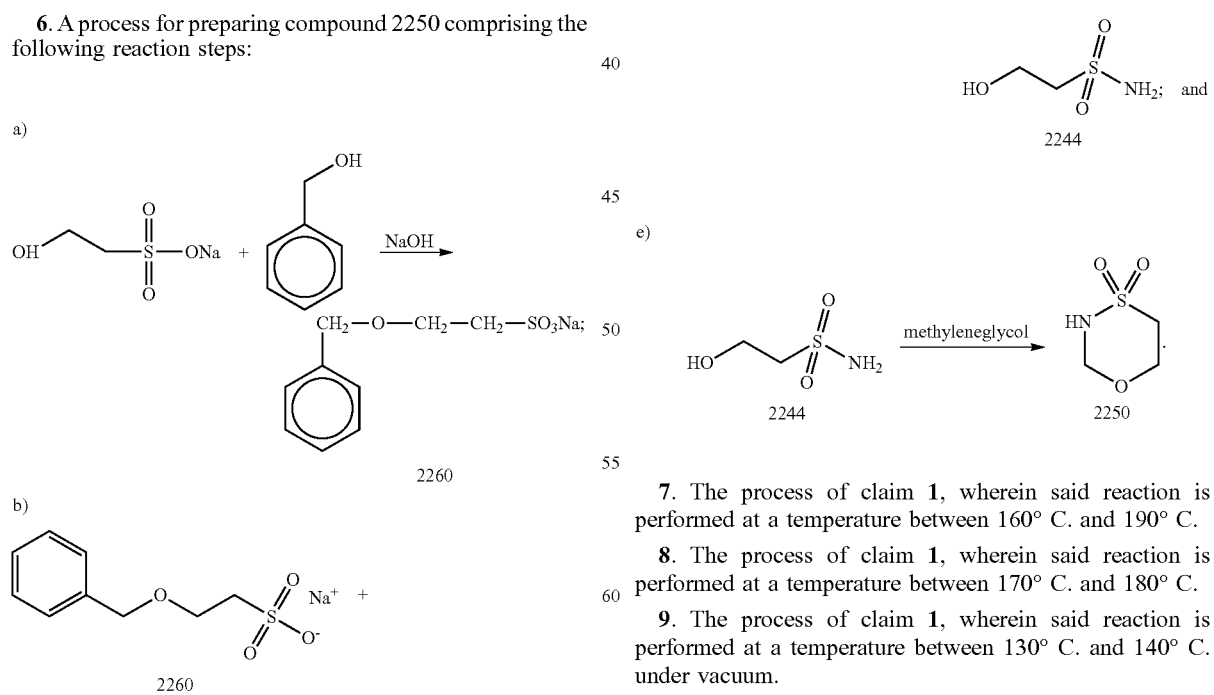
7. The process of claim 1, wherein said reaction is performed at a temperature between 160° C. and 190° C.
8. The process of claim 1, wherein said reaction is performed at a temperature between 170° C. and 180° C.
9. The process of claim 1, wherein said reaction is performed at a temperature between 130° C. and 140° C. under vacuum.
* * * * *